Figure 1:
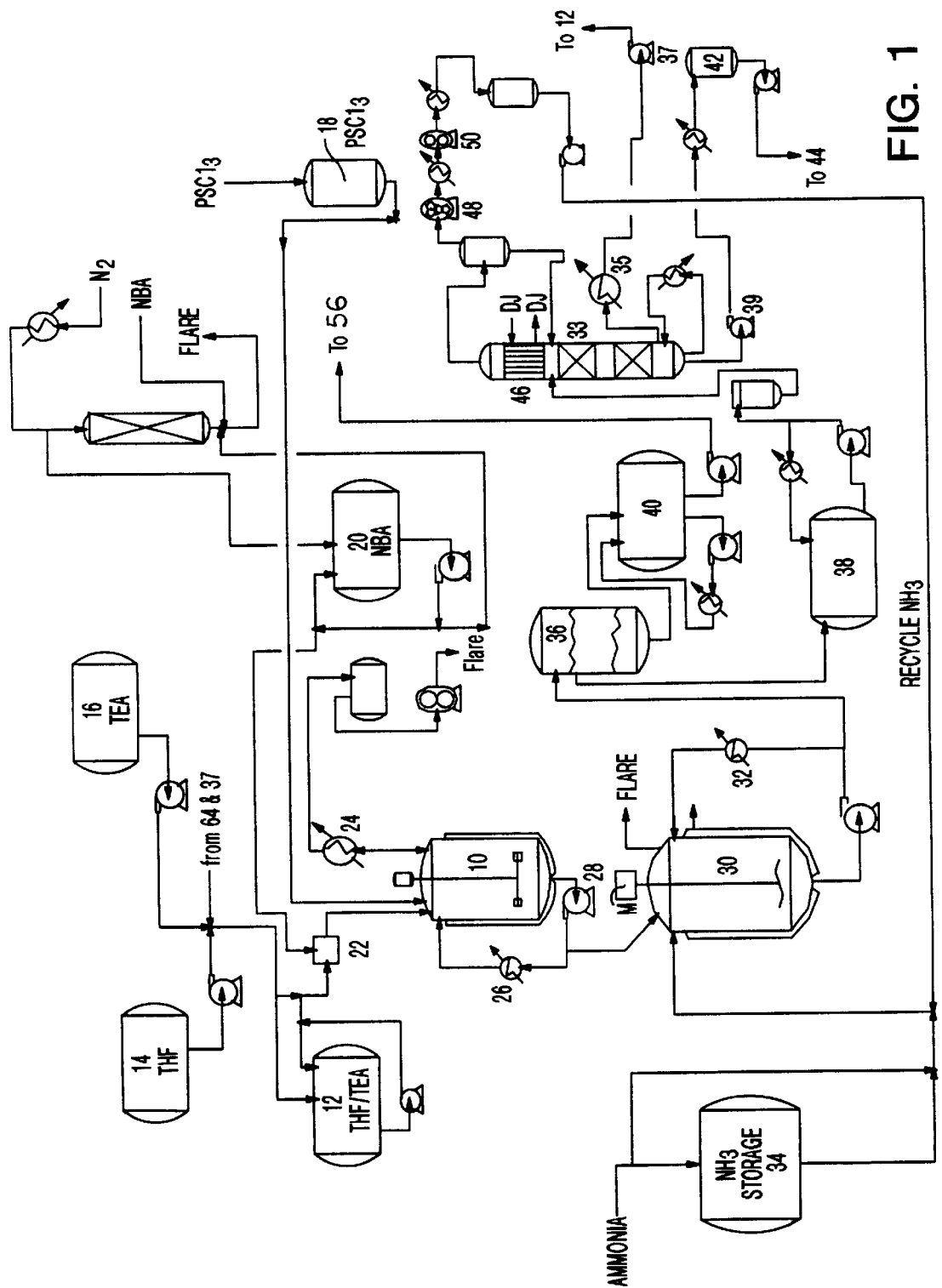

United States Patent [19]
Sulzer et al.

[11] Patent Number: 5,872,293
[45] Date of Patent: *Feb. 16, 1999

[54] SEPARATING AMMONIUM CHLORIDE FROM N-HYDROCARBYLPHOSPHORIC TRIAMIDE OR N-HYDROCARBYLTHIOPHOSPHORIC TRIAMIDE

[75] Inventors: Gerald M. Sulzer; Chi Hung Cheng, both of Baton Rouge, La.

[73] Assignee: Albemarle Corporation, Richmond, Va.

[ * ] Notice: The term of this patent shall not extend beyond the expiration date of Pat. No. 5,770,771.

[21] Appl. No.: 785,104

[22] Filed: Jan. 21, 1997

[51] Int. Cl.[6] .................................. C07F 9/44; C07F 9/24; C07F 9/201
[52] U.S. Cl. ................................................ 564/14
[58] Field of Search ................................. 564/14

[56] References Cited

U.S. PATENT DOCUMENTS

| | | | |
|---|---|---|---|
| 4,242,325 | 12/1980 | Bayless et al. | 424/210 |
| 4,530,714 | 7/1985 | Kolc et al. | 71/28 |

FOREIGN PATENT DOCUMENTS

| | | |
|---|---|---|
| 830800 | 3/1960 | United Kingdom . |
| 848952 | 9/1960 | United Kingdom . |

OTHER PUBLICATIONS

L. A. Cates; "Phosphorus–Nitrogen Compounds. XI. Phosphamidase Studies. I. Unsubstituted Amides[1,2]"; J. Med Chem., vol. 13, 1970; pp. 301–302.

M. Goehring, et al.; "Uber Phosphor–Stickstoffverbindungen, I. Mittell.: Zur Kenntnis der Amide der Phosphorasaure und der Thiophosphorsaure"; Chem. Ber., No. 7, 1956; pp. 1768–1774.

Kendall, et al; "Addition Compounds of Ammonia With The Ammonium Halides"; J. Amer. Chem. Soc., 1920, vol. 42; pp. 1141–1145.

Yamamoto, et al., "Measurement of Heat of Mixing for Ammonium Chloride + Ammonia System at 25°C"; The Canadian Journal of Chemical Engineering, vol. 66, 1988; pp. 127–130.

Abe, et al., "Regarding The Solubility of Di–And Trichlorides In Liquid Ammonia (Part 3) Solubility Of Ammonium Chloride And Vapor Pressure of Its Solution"; 1935; J. Soc. Chem. Ind. Japan, vol. 38, pp. 1402–1406.

*Primary Examiner*—Peter O'Sullivan
*Attorney, Agent, or Firm*—Philip M. Pippenger

[57] ABSTRACT

A substantially anhydrous mixture which comprises ammonium chloride, the triamide, and ammonia is formed either by adding ammonia to a mixture of the other components or by conducting, in the presence of the ammonia and an organic solvent, a reaction to form the triamide and ammonium chloride as co-products. In all cases the ammonia is present in a sufficient excess amount relative to the ammonium chloride to form a separate liquid phase in which the ammonium chloride solids dissolve. Such separate liquid phase is separated from the remainder of said mixture.

21 Claims, 2 Drawing Sheets

SEPARATING AMMONIUM CHLORIDE FROM N-HYDROCARBYLPHOSPHORIC TRIAMIDE OR N-HYDROCARBYLTHIOPHOSPHORIC TRIAMIDE

BACKGROUND

N-hydrocarbylphosphoric triamides and N-hydrocarbylthiophosphoric triamides are known to be effective urease inhibitors for use with urea-based fertilizer compositions. See, for example, U.S. Pat. No. 4,530,714 to J. F. Kole, et al.

Known procedures for preparing such triamides involve operations in which N-hydrocarbylaminophosphoryl dichloride (also known as N-hydrocarbylphosphoramidic dichloride) or N-hydrocarbylaminothiophosphoryl dichloride (also known as N-hydrocarbylthiophosphoramidic dichloride) is formed in a first reaction, recovered, and often purified. In a second reaction, the N-hydrocarbylaminophosphoryl dichloride or N-hydrocarbylaminothiophosphoryl dichloride is reacted with ammonia to produce a slurry from which co-product ammonium chloride is separated by filtration. See for example, U.S. Pat. No. 4,530,714.

Filtration of the co-product ammonium chloride from the reaction product mixture can be a difficult and time-consuming operation, especially if the process is being conducted on a large scale in commercial-type production facilities. A desirable contribution to the art would be a process wherein the filtration of co-product ammonium chloride formed in the production of N-hydrocarbylphosphoric triamides or of N-hydrocarbylthiophosphoric triamides can be eliminated. An additional desirable contribution would be to enable formation of a useful liquid co-product mixture containing the ammonium chloride formed in the process.

The $NH_4Cl$ and $NH_3$ binary system has been discussed in the literature. See, for example, Hideki Yamamoto, Seiji Sanga, and Junji Tokunaga, *The Canadian Journal of Chemical Engineering*, Vol. 66, February 1988, pp 127–130 ("Measurement of Heat of Mixing for Ammonium Chloride+Ammonia at 25° C."); James Kendall and J. G. Davidson, *J. Am. Chem. Soc.* 1920, Vol. 42, pp 1141–1145 ("Addition Compounds of Ammonia with the Ammonium Halides"); and Sueyoshi Abe, Kyozo Watanabe, and Tatsusaburo Hara, *J. Soc. Chem. Ind. Japan,* 1935, Vol, 38, pp 1402–1406 ("Solubilities and Vapor Pressures of $NH_4Cl+NH_3$ System").

THE INVENTION

In accordance with this invention, novel process technology is provided which eliminates the need for filtration of the co-product ammonium chloride formed in the production of N-hydrocarbylthiophosphoric triamides. In addition, this invention makes it possible, pursuant to a preferred embodiment, to form a useful liquid co-product mixture containing the ammonium chloride formed in the process.

One embodiment of this invention is a process for separating ammonium chloride from a triamide of the formula

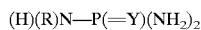

where R is a hydrocarbyl group and Y is an atom of oxygen or sulfur. The process comprises (i) forming a substantially anhydrous mixture composed of the triamide, ammonium chloride, and ammonia, the ammonia being present in a sufficient amount relative to the ammonium chloride so that a separate liquid phase forms containing ammonia and the ammonium chloride, and (ii) separating such liquid phase from the remainder of the mixture. Substantially all of the triamide stays in the remainder of the mixture from which the separate liquid phase has been separated. For ease of reference, the separate liquid phase containing the ammonia and the ammonium chloride is sometimes referred to hereinafter as the ammoniate phase.

It has been found that the ammoniate phase (which is predominately inorganic) and the remainder of the initial mixture (which is predominately organic) are easily separated from each other, for example by a gravity separation (e.g., draining off the lower layer or by siphoning or otherwise drawing off the upper layer), or by use of other known procedures for separating one liquid phase from another.

Typically the initial mixture further includes one or more substantially anhydrous organic solvents. When such solvent is present, all except small impurity amounts thereof (e.g., less than about 0.5 wt. %) will stay in the remainder of the mixture upon effecting the separation of the ammoniate phase from the remainder of the initial mixture. Thus in such case the remainder of the mixture from which the ammoniate phase has been separated, comprises substantially all of the triamide as well as substantially all of the solvent.

The above process can be performed in various ways. In one such embodiment of the invention, a sufficient amount of ammonia is mixed with a combination or preformed mixture of the ammonium chloride and the triamide such that the ammoniate phase is produced. Then the separation is carried out. The amount of ammonia used in this embodiment should be at least about 2.8–10.0 moles of ammonia (depending on the amount of solvent(s) present; the more the solvent, the more the amount of ammonia should be) per mole of ammonium chloride.

Another embodiment comprises co-producing the triamide and the ammonium chloride in the presence of excess ammonia so that the ammoniate phase forms during the process, and then separating the ammoniate phase from the remainder of the mixture. A preferred process for co-producing the triamide and the ammonium chloride in accordance with this embodiment involves reacting N-hydrocarbylaminophosphoryl dichloride or N-hydrocarbylaminothiophoshoryl dichloride with a sufficient excess amount of ammonia (e.g., at least about 16 moles and preferably at least about 20 moles of ammonia per mole of the dichloride reactant) to produce the triamide and concurrently form the separate ammoniate phase. In theory, there is no upper limit on the amount of ammonia used as the excess ammonia does not materially interfere with the desired reactions. Thus the amount of excess ammonia above the foregoing minimum amounts is largely a matter of common sense and practicality; i.e., the larger the excess, the larger the amounts of ammonia that need to be recovered and recycled.

Still another embodiment of this invention comprises reacting N-hydrocarbylaminophosphoryl dichloride or N-hydrocarbylaminothiophosphoryl dichloride with incrementally added portions of ammonia so that during and/or after the triamide has been formed, the separate liquid ammoniate phase is formed. The ammoniate phase can be removed incrementally as it is formed or after all of it has been formed.

The temperature of the preformed mixture of triamide, ammonium chloride and organic solvent to which the ammonia is being added, should be maintained above about 6° C. but below the temperature at which the triamide undergoes significant thermal degradation. Likewise, the temperature of the mixture in which the triamide and ammonium chloride are being co-produced in a suitable organic solvent by reaction between (a) N-hydrocarbylaminophosphoryl dichloride or N-hydrocarbylaminothiophosphoryl dichloride and (b) a suitable amount of initially added and/or incrementally added ammonia should also be maintained above about 6° C. but below the temperature at which the triamide undergoes significant thermal degradation. At temperatures of about 6° C. and below, an ammonia-ammonium chloride complex forms as a solid phase which can cause pluggage of reaction equipment and which in any event detracts from the efficiency of the overall operation. Thus such low temperatures should be avoided. The thermal degradation temperatures of the triamides usually differs at least to some extent from compound to compound, and thus the maximum permissible temperature may vary from compound to compound. In general, however, significant thermal degradation of the triamides is not incurred at temperatures of up to about 50° C. and in some cases perhaps not until up to still higher temperatures.

Another embodiment of this invention is a process for the preparation of N-hydrocarbylphosphoric triamide or N-hydrocarbylthiophosphoric triamide, which process comprises:

a) mixing in at least one inert liquid organic solvent, and in the presence of an HCl acceptor, preferably a tertiary amine) (i) N-hydrocarbylaminophosphoryl dichloride or N-hydrocarbylaminothiophosphoryl dichloride and (ii) ammonia in proportions (1) that are at least about 16 moles of ammonia per mole of said dichloride, (2) that produce a reaction mixture containing N-hydrocarbylphosphoric triamide or N-hydrocarbylthiophosphoric triamide (as the case may be), and (3) that keep in solution as a separate liquid phase substantially all of the ammonium chloride co-product formed in the reaction, and removing heat of reaction from the mixture so-formed at a rate of removal such that the temperature of the reaction mixture remains high enough to keep ammonium chloride-ammonia complex from forming an appreciable amount of solid phase in said reaction mixture, but low enough to avoid significant reduction in yield of N-hydrocarbylthiophosphoric triamide; and b) separating said separate liquid phase from the remainder of said mixture.

If in any special case where chemical or other considerations require or involve running the reaction at ≦6° C., this embodiment of the invention can be modified to conduct the reaction at the lower temperature where the solid ammonia/ammonium chloride complex forms, and heating the final reaction mass above 6° C. to melt the complex thus forming the separate liquid ammoniate phase to allow phase separation and removal.

When producing N-hydrocarbylthiophosphoric triamides it is most desirable to utilize a continuous process which includes, inter alia, the separation process of this invention. The continuous process is described in commonly-owned copending U.S. application Ser. No. 08/786,396, filed Jan. 21, 1997, all disclosure of which is incorporated herein by reference. Pursuant to this invention, a continuous process which includes the above separation process comprises:

a) continuously feeding and mixing in a reaction chamber (i) N-hydrocarbylaminothiophosphoryl dichloride, (ii) a substantially anhydrous organic solvent in which said dichloride is soluble, and (iii) ammonia in proportions (1) that are at least about 16 moles (preferably at least 20 moles) of ammonia per mole of N-hydrocarbylaminothiophosphoryl dichloride, (2) that produce a reaction mixture containing N-hydrocarbylthiophosphoric triamide, and (3) that keep in solution substantially all of the ammonium chloride co-product formed in the reaction, and removing heat of reaction from the mixture formed in a) at a rate of removal such that the temperature of the reaction mixture remains high enough to keep ammonium chloride-ammonia complex from forming an appreciable amount of solid phase in such reaction mixture, but low enough to avoid significant reduction in yield of N-hydrocarbylthiophosphoric triamide;

b) withdrawing effluent from the foregoing reaction chamber at a rate sufficient to maintain a substantially constant volume of reaction mixture therein;

c) forming or allowing to form in the effluent from the reaction chamber a separate liquid phase containing ammonia and the ammonium chloride; and d) separating such liquid phase from the remainder of the mixture, preferably by use of gravity as described above.

The effluent withdrawn in b) of the immediately preceding sentence is caused/allowed in c) hereinabove to separate into a predominately inorganic phase comprising ammonia and ammonium chloride (usually with a small amount of co-product thiophosphoric triamide), and a predominately organic phase comprising N-hydrocarbylthiophosphoric triamide, and solvent (usually together with dissolved ammonia). The separation of d) hereinabove is readily conducted, even on a large scale.

As described in the aforesaid application Ser. No. 08/786, 396, filed Jan. 21, 1997, it is most preferred to produce the N-hydrocarbylaminothiophosphoryl dichloride by continuously feeding to and mixing in a first reaction chamber (i) a preformed mixture of a hydrocarbyl primary amine (preferably an alkyl amine), tertiary amine (preferably triethylamine), and at least one liquid inert organic solvent (most preferably a cyclic ether, especially tetrahydrofuran), and (ii) thiophosphoryl chloride and remove heat of reaction at a rate sufficient to maintain the temperature of the reaction mixture in the range of about −20° to about +50° C., to produce a reaction mixture containing N-hydrocarbylaminothiophosphoryl dichloride and solvent. This reaction mixture can be used as feed to a) of the immediately preceding paragraph.

The above and other embodiments of this invention will be apparent from the ensuing description, accompanying drawings, and appended claims.

THE DRAWINGS

Figure 2:
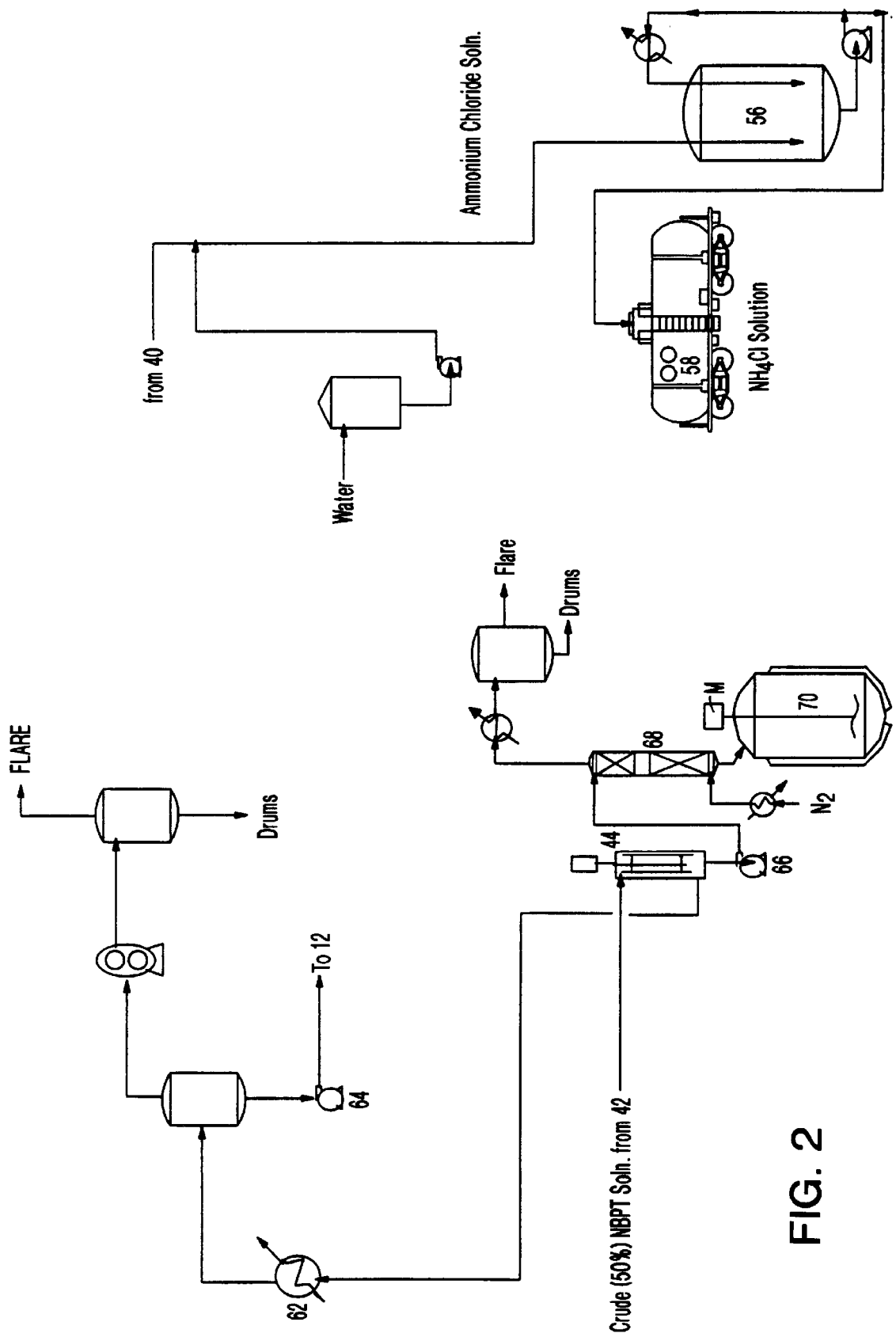

FIGS. 1 and 2, taken together, constitute a schematic representation of a preferred overall installation and the process flows for the production and purification of N-hydrocarbylaminothiophosphoryl dichloride on a continuous basis.

FIG. 1 schematically depicts the preferred installation and flow streams for the two-stage reactions used in the process.

FIG. 2 schematically depicts the preferred installation and flow streams for the workup and recovery of products formed in the operation of the installation of FIG. 1.

FURTHER DETAILED DESCRIPTION

As noted above, at least one liquid, inert, substantially anhydrous organic solvent is preferably employed in the various embodiments of this invention. While any solvent meeting these criteria can be used, it is preferred to use a solvent that boils at one or more temperatures in the range of about 40° to about 120° C. and preferably in the range of about 55° to about 90° C. at ordinary atmospheric pressures. Thus use can be made of liquid paraffinic, cycloparaffinic, and/or aromatic hydrocarbons, liquid halocarbons and halohydrocarbons, ethers, esters, and other organic liquids which do not interfere with the desired reactions or operations. Ethers, especially cyclic ethers such as 1,4-dioxane, 1,3-dioxolane, tetrahydrofuran, methyltetrahydrofuran, and tetrahydropyran, are preferred. Preferably the solvent is subsequently recovered, most preferably by one or more flash distillations, and is reused in the process.

Of the various suitable solvents, tetrahydrofuran is particularly preferred because of its good solvency properties, desirable boiling point, ready availability and low cost.

The triamides separated from ammonium chloride or produced and separated from ammonium chloride pursuant to this invention have the formula:

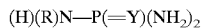

$(H)(R)N-P(=Y)(NH_2)_2$ where R is a hydrocarbyl group and Y is an atom of oxygen or sulfur. The hydrocarbyl group can be any hydrocarbyl group such as, for example, alkyl, cycloalkyl, alkenyl, cycloalkenyl, alkynyl, aryl, aralkyl, or cycloalkylalkyl group. Typically the hydrocarbyl group will contain up to about 20 carbon atoms, and preferably up to about 10 carbon atoms. Preferably R is an alkyl group containing up to about 10 carbon atoms and more preferably, in the range of from about 4 to about 8 carbon atoms. Y is preferably a sulfur atom. A particularly preferred triamide in the practice of this invention is N-n-butylthiophosphoric triamide. In the embodiments of this invention wherein the excess ammonia is added during the co-production of the triamide and ammonium chloride, ammonia is reacted with an N-hydrocarbylaminophosphoryl dichloride or N-hydrocarbylaminothiophosphoryl dichloride of the formula:

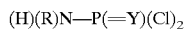

$(H)(R)N-P(=Y)(Cl)_2$ where R and Y are as described above. A tertiary amine is used as an acid acceptor for the by-product HCl formed in the reaction to form these dichlorides. It is not consumed by the process and is converted back to the free amine by ammonia. In the preferred method for making N-hydrocarbylthiophosphoric triamides, the complete reaction mass from the dichloride reaction, which includes the tertiary amine HCl salt, is fed to the triamide reactor. Therefore, embodiments of this invention that feed the excess ammonia during the co-production of the triamide and ammonium chloride will usually have the tertiary amine present as a solvent in the separated organic phase. Suitable tertiary amines for the dichloride reaction and which would appear in the embodiments of this invention include heterocyclic tertiary amines such as 3-picoline (bp ca. 143°–144° C.), 4-picoline (bp ca. 143° C.), 4-chloropyridine (bp ca. 147°–148° C.), 3-ethylpyridine (bp ca. 165°–166° C.), and 4-ethylpyridine (bp ca. 166° C.), and trialkylamines such as tripropylamine (bp ca. 155°–158° C.), and tri-sec-butylamine (bp ca. 191°–192° C.). Relatively low boiling tertiary amines such as pyridine (bp ca. 115° C.), 2-picoline (bp ca. 128° C.), N,N-diethylmethylamine (bp 63°–65° C.), and triethylamine (bp ca. 89° C.) are preferred. From a cost-effectiveness standpoint, triethylamine is a particularly preferred tertiary amine.

Typically, the separated and recovered inorganic phase (chiefly composed of ammonia and ammonium chloride) is first diluted with water to make the product easier to handle and a more useable form for the end use. Preferably, the water added is proportioned to yield a co-product solution containing about 25% water, about 38% dissolved ammonium chloride and about 37% ammonia. Such a composition makes a product useful for neutralization of industrial waste water. Further dilution with water to a composition that yields a total nitrogen content in the 20–25 wt. % range produces a product that is suitable for direct application as a nitrogen fertilizer. In order to suit other specific industrial uses for the ammonia and ammonium chloride co-products, the amount of water added can be varied, and in fact, the addition of water can be entirely eliminated if desired.

The results of comparative experiments set forth in the following illustrative Example demonstrate the effectiveness and advantageous character of the separation process of this invention. This Example is not intended to limit the scope of this invention.

EXAMPLE

The reactor used in these experiments was a 1-liter high pressure glass reactor equipped with a cooling coil, a mechanical agitator and dip legs for introducing solvents and reactants into the reactor. First, thiophosphoryl chloride was charged to the reactor. Some tetrahydrofuran (THF) was added to the reactor in order to raise the liquid level above the agitator blades. Triethylamine (TEA) and n-butyl amine (NBA) were premixed in tetrahydrofuran and slowly fed to the thiophosphoryl trichloride/tetrahydrofuran mixture in the reactor. The reactor temperature was kept around 50° F. (ca. 10° C.) during the addition. Upon completion of this reaction wherein N-n-butylaminothiophosphoryl dichloride (BAPTD) was produced, liquid ammonia was added as fast as possible to the BAPTD reaction mass. The ammonia addition took about 15–20 minutes to complete. Reactor temperature was again maintained at about 50° F. (ca. 10° C.) during the addition. At the end of the ammonia feed, reactor pressure was 25–30 psig. The reaction resulted in the formation of a reaction mass containing as the principal products, N-n-butylthiophosphoric triamide (BTPT) and ammonium chloride co-product. The final concentration of BTPT in the reaction solution from this second reaction was 7–8 wt. %.

In comparative Run B, representing practice of prior art, the ammonia to BAPTD ratio (7.24:1) was only slightly above the stoichiometric amount required to complete reaction and saturate the organic reaction mass at the reaction pressure. Use of this ammonia ratio caused the NH$_4$Cl to form as a solid. At the end of the reaction, the excess ammonia was vented and the NH$_4$Cl solids were filtered and washed with the wash being added back to the filtrate. The BTPT product was recovered from the combined filtrates by evaporation of the tetrahydrofuran solvent.

In Run A, representing the practice of this invention, an ammonia:BAPTD ratio of 24.6:1 was used to effect the formation of a separate ammoniate phase. Following reaction, the ammoniate phase was allowed to phase separate and the organic phase was separated from the ammoniate phase. The organic phase was then vented to release dissolved ammonia and BTPT was again recovered by evaporation of the tetrahydrofuran solvent. A summary of the results is presented in the Table. In addition to the greater ease of ammonium chloride removal made possible by this invention, improvements in BTPT purity and in BTPT yield were achieved by the practice of this invention.

TABLE

| Experiment | Mole Feed Ratios, NBA:TEA:NH$_3$:PSCl$_3$ | BTPT Purity, wt % | BTPT Yield, % on P |
|---|---|---|---|
| Run A | 1.02:1.04:24.6:1 | 88.7 | 87.2 |
| Run B | 1.02:1.02:7.24:1 | 85.0 | 82.2 |

In the embodiments of this invention wherein the triamide is produced as well as separated from the co-produced ammonium chloride, ammonia is reacted with an N-hydrocarbylaminophosphoryl dichloride or N-hydrocarbylaminothiophosphoryl dichloride of the formula:

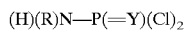

where R and Y are as described above.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

ADDENDUM

In the exercise of a superabundance of caution, for purposes of satisfying best mode requirements as interpreted from time to time by the courts, the following addendum is provided dealing with the continuous process of commonly-owned copending U.S. application Ser. No. 08/786,396, filed Jan. 21, 1997, in which the separation and recovery process of this invention can be, and preferably is, employed.

Reactants

The principal reactants in the process are primary hydrocarbyl monoamine, thiophosphoryl chloride (PSCl$_3$), and ammonia. The hydrocarbyl group of the primary amine reactant can be any hydrocarbyl group such as alkyl, cycloalkyl, alkenyl, cycloalkenyl, alkynyl, aryl, aralkyl, or cycloalkylalkyl group. Typically the hydrocarbyl group will contain up to about 20 carbon atoms, and preferably up to about 10 carbon atoms. Of such compounds monoalkyl amines, monocycloalkylamines and monoarylamines are preferred, and of these, monoalkyl amines having 2 to 6 carbon atoms in the molecule are especially preferred. Most preferred as the amine reactant is n-butylamine.

The ammonia is preferably stored and handled in its liquid form. However, gaseous ammonia, or mixtures of gaseous and liquid ammonia, can also be used, if desired.

Solvent

At least one liquid inert organic solvent is employed in the process. While any solvent meeting these criteria can be used, it is preferred to use a solvent that boils at one or more temperatures in the range of about 40° to about 120° C. and preferably in the range of about 55° to about 90° C. at ordinary atmospheric pressures. Thus use can be made of liquid paraffinic, cycloparaffinic, and/or aromatic hydrocarbons, liquid halocarbons and halohydrocarbons, ethers, esters, and other organic liquids which do not interfere with the desired reactions. Ethers, especially cyclic ethers such as 1,4-dioxane, 1,3-dioxolane, tetrahydrofuran, methyltetrahydrouran, and tetrahydropyran, are preferred. Preferably the solvent is recovered, most preferably by one or more flash distillations, and is used as recycle in the process.

Of the various suitable solvents, tetrahydrofuran is particularly preferred because of its good solvency properties, desirable boiling point, ready availability and low cost. In a well-designed facility, about 99% of the tetrahydrofuran can be recovered, and preferably the recovered tetrahydrofuran is used as recycle in the process.

HCl Acceptor

A tertiary amine is used as an acid acceptor for the by-product HCl formed in the first reaction. It is not consumed by the process, and in the preferred embodiments the tertiary amine is recycled in the process. Suitable tertiary amines include heterocyclic tertiary amines such as 3-picoline (bp ca. 143°–144° C.), 4-picoline (bp ca. 143° C.), 4-chloropyridine (bp ca. 147°–148° C.), 3-ethylpyridine (bp ca. 165°–166° C.), and 4-ethylpyridine (bp ca. 166° C.), and trialkylamines such as tripropylamine (bp ca. 155°–158° C.), and tri-sec-butylamine (bp ca. 191°–192° C.). Relatively low boiling tertiary amines such as pyridine (bp ca. 115° C.), 2-picoline (bp ca. 128° C.), N,N-diethylmethylamine (bp 63°–65° C.), and triethylamine (bp ca. 89° C.) are preferred.

From a cost-effectiveness standpoint, triethylamine is a particularly preferred tertiary amine. In a well-designed facility for the continuous process, about 99% of the triethylamine can be recovered, and preferably the recovered triethylamine is used as recycle in the process. Thus the process is capable of producing suitably high purity product (s) while at the same time being both highly efficient and environmentally friendly.

Reaction Conditions

The first stage reaction involving reaction between thiophosphoryl chloride and the primary amine is typically conducted at one or more temperatures in the range of about −20° to about 50° C., and preferably at one or more temperatures in the range of about 0° to about 15° C. The pressure conditions for this reaction are not important unless evaporative cooling is used to control reactor temperature. If using evaporative cooling, the reactor pressure is controlled such that the reaction mass will boil at the desired reactor temperature. Proportions of reactants in the first stage are essentially equimolar, and the mole ratio of primary amine to thiophosphoryl chloride is typically in the range of about 0.95 to about 1.1 moles of amine per mole of the $PSCl_3$. For best results, the mole ratio of primary amine to thiophosphoryl chloride is in the range of about 1.00 to about 1.05 moles of amine per mole of the $PSCl_3$.

The desired product of the first stage reaction is an N-hydrocarbylaminophosphoryl dichloride. Such compounds have the formula, $(H)(R)N—P(=S)Cl_2$, where R is a hydrocarbyl group.

As noted above, primary hydrocarbyl monoamine and tertiary amine are charged to the first reaction chamber as a preformed mixture which also includes one or more solvents, and the proportions of primary hydrocarbyl monoamine and tertiary amine in such preformed mixture are typically in a molar ratio range of about 1:1 to about 1:1.5 respectively. Typically, the proportions of such preformed mixture and the thiophosphoryl chloride fed to the first reaction chamber are such that per mole of thiophosphoryl chloride there are in the range of about 0.95 to about 1.1 moles of primary hydrocarbyl monoamine and in the range of about 0.95 to about 1.5 moles of tertiary amine.

In the second stage reaction between the N-hydrocarbylaminothiophosphoryl dichloride and ammonia, one or more temperatures in the range of about 5° to about 50° C. and one or more pressures in the range of about 15 to about 100 psig are typically employed, with the proviso that in any given situation, the temperature is high enough to keep the co-product ammonium chloride-ammonia complex in solution, yet low enough to avoid significant reduction in yield (e.g., a loss of more than 5 wt. % yield) of N-hydrocarbylthiophosphoric triamide. The N-hydrocarbylthiophosphoric triamides have the formula, $(H)(R)N—P(=S)(NH_2)_2$, where R is a hydrocarbyl group. Preferred conditions for the second stage reaction, especially when producing N-n-butylthiophosphoric triamide involve one or more temperatures in the range of about 8° to about 15° C. and one or more pressures in the range of about 25 to about 40 psig. In the second stage reaction the proportions of ammonia to the N-hydrocarbylaminothiophosphoryl dichloride are such that there are at least about 16 moles of ammonia, and preferably at least about 20 moles of ammonia, per mole of N-hydrocarbylaminothiophosphoryl dichloride. In theory there is no upper limit on the amount of ammonia used as the excess ammonia does not materially interfere with the desired reactions. Thus the amount of excess ammonia above the foregoing minimum amounts is largely a matter of common sense and practicality; i.e., the larger the excess, the larger the amounts of ammonia that need to be recovered and recycled.

The amount of solvent used in the process is an amount sufficient to provide a suitably fluid reaction medium, and thus is largely a matter of choice, common sense, and practicality.

Thus unduly excessive amounts of solvent should be avoided as the larger the amount used, the larger the amount that needs to be recovered and recycled.

The first stage and the second stage reactions are both exothermic reactions and thus suitable equipment should be provided to ensure that adequate cooling capacity is available for each of the two stages. In a preferred embodiment, the heat of reaction from the first stage reaction mixture is removed by continuously circulating a portion of that reaction mixture from the first stage reaction chamber into a heat exchanger where heat is removed by a cooling medium, and thence back to the first reaction chamber. In a particularly preferred embodiment the heat of reaction from the first stage reaction mixture is removed by controlling the pressure such that the reaction mixture boils and the vapors from the boiling mixture are condensed in a dephlegmator heat exchanger and refluxed back to the first reaction chamber.

In another preferred embodiment the reaction mixture in the first reaction chamber is continuously stirred or agitated by a mechanical stirrer or agitator, and the preformed mixture and the thiophosphoryl chloride are both fed into such reaction mixture below the surface thereof and in close proximity to the stirrer/agitator to ensure prompt and rapid mixing of these feeds.

In still another preferred embodiment, the heat of reaction from the second stage reaction mixture is removed by continuously circulating a portion of that mixture through a heat exchanger and thence back to the second reaction chamber.

Alternatively, the first and the second reaction chambers are both heat exchangers that provide a residence time in the range of 1 to about 10 minutes and that provide sufficient heat exchange surface in contact with the reaction mixture therein to enable removal of the heat of reaction generated within such residence time.

Effluent from the second reaction chamber is withdrawn at a rate sufficient to maintain a substantially constant volume of reaction mixture in the second reaction chamber, and preferably, the effluent from the first reaction chamber is withdrawn therefrom and fed to the second reaction chamber at a rate that maintains a substantially constant volume of reaction mixture in the first reaction chamber.

Preferably, the effluent from the second reaction chamber is caused/allowed to separate into (A) an inorganic phase comprising predominately ammonia, ammonium chloride and co-product thiophosphoric triamide, and (B) an organic phase comprising predominately N-hydrocarbylthiophosphoric triamide, tertiary amine, solvent and dissolved ammonia, and the resultant phases are separated from each other. This is preferably accomplished by allowing the effluent to stand in a quiescent state for a suitable period of time for the distinct separate phases to form and then draining off the lower layer. Other separation techniques such as siphoning off the top layer, use of emulsion breakers, and like procedures can be used whenever deemed necessary or desirable. After effecting this separation, it is preferred to separate ammonia along with a portion of the solvent from the isolated organic phase, and compress and cool this ammonia-solvent mixture to form a recycle mixture of liquid ammonia and solvent. This separation also provides as the residual mixture, a concentrated product mixture comprising predominately N-hydrocarbylthiophosphoric triamide, and residual solvent and tertiary amine. The recycle mixture of ammonia and the solvent remaining therewith is recycled for use as a portion of the ammonia feed to the second reaction chamber.

The concentrated product mixture is then processed so as to separate and recover tertiary amine and solvent therefrom, and the tertiary amine and solvent collected therewith are recycled for use as a portion of the feed for making the preformed mixture to be fed to the first reaction chamber. The residual portion of the organic phase remaining after this separation comprises N-hydrocarbylthiophosphoric triamide, and only small residual amounts of solvent and tertiary amine. Thereupon the N-hydrocarbylthiophosphoric triamide and the small residual amounts of solvent and tertiary amine are separated from each other to yield a purified N-hydrocarbylhiophosphoric triamide product. Either or both of this separated residual solvent and tertiary amine is/are recycled for use as a portion of the feed for making the preformed mixture fed to the first reaction chamber.

The specific techniques used for effecting the foregoing separations will depend to some extent upon the identities of the materials making up the mixtures being processed. Usually distillations or flash distillations will be employed whenever this is feasible. However, in any case where such distillation procedures are not feasible because of the properties of the materials being processed, recourse may be had to other separation techniques such as solvent extraction procedures, chromatographic separation procedures, or the like.

Reference will now be made to the continuous process depicted in FIGS. 1 and 2.

First Stage Reaction

In the embodiment depicted in FIGS. 1 and 2, triethylamine (TEA) and tetrahydrofuran (THF) are fed to the first reactor 10 as a mixture from a recycle solvent tank 12. Make-up THF and TEA stored in tanks 14 and 16, respectively, are added to recycle tank 12 as needed to maintain a constant solvent composition going to reactor 10. The feed rate is determined by maintaining a constant feed ratio of TEA to $PSCl_3$, based on periodic analyses of TEA in the TEA/THF mixture. This analysis should have +/−400 ppm (or better) resolution to allow control of the TEA/$PSCl_3$ mole ratio within 1–2% of target (1.10+/−0.02). TEA is consumed in this first reaction step and regenerated in the second reaction, while THF acts only as a solvent.

In first reactor 10, $PSCl_3$ (mass flow controlled) is reacted with n-butylamine (NBA) to form N-n-butylaminothiophosphoryl dichloride (BATPD) intermediate. The NBA is stored in tank 20 under nitrogen. Two different streams are fed to the reactor: 1) neat $PSCl_3$ from tank 18; and 2) mixed feeds of recycle THF/TEA and NBA from static mixer 22. The NBA feed rate is proportioned to the $PSCl_3$ feed rate to maintain a mole ratio of approximately 1.01 moles of NBA per mole of $PSCl_3$ and the THF/TEA feed rate is proportioned to the $PSCl_3$ feed rate to maintain a mole ratio of approximately 1.10 moles of TEA per mole $PSCl_3$.

Mixing is considered highly important for achieving very high efficiency in this reaction, and thus the NBA and THF/TEA are combined in static mixer 22 upstream of the reactor, and introduced to the reactor through a dip leg just above the agitator. The $PSCl_3$ is fed neat through a separate dip leg into the same area of the reactor. The HCl formed as co-product reacts with the TEA to form a TEA•HCl salt which precipitates from the reaction mass.

The reaction to form this intermediate BATPD is very exothermic, and most of this heat of reaction is removed by refluxing the THF solvent in a dephlegmator 24. Recommended reaction conditions in reactor 10 are 0°–15° C. and, to allow solvent reflux, about 40–70 mm Hg (0.8–1.4 psia) pressure. Feed rates are adjusted to provide a three hour residence time in reactor 10. Since this reaction is very fast (1–2 minutes maximum) and irreversible, holdup in this reactor simply provides surge capacity for the process. Additional cooling for the reaction is provided by the reactor jacket and a pump-around loop through heat exchanger 26. The reaction mass discharge is fed continuously to the second reactor 30 via level control on first reactor 10.

Second Stage Reaction

In the second reactor 30, the intermediate BATPD from reactor 10 reacts with ammonia to give the final product, N-(n-butyl)thiophosphoric triamide (BTPT). The HCl generated by the reaction also reacts with ammonia to form ammonium chloride, and the TEA•HCl also reacts with ammonia to liberate the TEA and form additional ammonium chloride. A total of 5 moles of ammonia per mole BATPD is consumed in this step. This reaction is very exothermic, and the heat of reaction is removed via a pump-around loop through heat exchanger 32. Reaction conditions for reactor 30 are 8°–15° C. and 25–38 psig, and the residence time is about 90 minutes.

Ammonia is fed by pressure control to reactor 30, and the ammonia feed consists of the recycle stream from product phase column 33 and fresh ammonia from storage vessel 34. A total of about 23–25 moles of ammonia per mole of BATPD is fed to reactor 30. Of this, about 14 moles is fresh ammonia. In order to keep the ammonium chloride co-product in solution, this amount of excess ammonia is used so that the ammonium chloride and the ammonia form a separate liquid phase containing about three moles of ammonia per mole of ammonium chloride. At lower ammonia levels, the ammonium chloride precipitates from the solution, forming a slurry which tends to cause pluggage problems. If the temperature in reactor 30 is allowed to go below about 6° C., the ammonium chloride/ammonia complex ($NH_4Cl \cdot 3NH_3$) will precipitate, which can also cause pluggage problems. Effluent discharge from this reactor is controlled to maintain constant level in reactor 30, and is sent to phase separator 36.

Phase Separation

The reaction mass coming from reactor 30 separates into two phases in phase separator 36, namely, (A) an inorganic phase containing ammonia, ammonium chloride, most of the by-product thiophosphoric triamide (TPT), and small amounts (<1%) of BTPT, THF and TEA; and (B) an organic phase containing THF, TEA, BTPT, some of the TPT, the other phosphorus by-product impurities, and ammonia. These are separated by gravity in separator 36 by employing a residence time therein of approximately 45 minutes. The separated phases are then stored, respectively, in two vessels, vessel 38 for the organic phase mixture and vessel 40 for the inorganic phase mixture. All three of these vessels (separator 36, and vessels 38 and 40) are maintained at the same pressure (40–50 psig) to allow gravity flow, and are cooled to hold a constant temperature (and thus constant composition and pressure). In the preferred system depicted, make-up ammonia can be fed directly to any of these drums from storage vessel 34, if the ammonia concentration becomes low enough to cause ammonium chloride precipitation.

Organic Phase Distillation

The organic phase from vessel 38 is first distilled in product phase column 33 to remove dissolved ammonia and most of the solvents, i.e., THF and TEA. The ammonia stream (which contains about 25% THF) is recycled directly to the second stage reaction in reactor 30; the combined THF and TEA solvents are taken as a vapor side-stream from the column sump, condensed in condenser 35, and transferred via pump 37 to recycle solvent tank 12. The concentrated (bottoms) product solution (containing about 50% THF) is transferred to feed drum 42.

Column 33 is operated at about 7–8 psia pressure and 55° C. bottoms temperature to minimize thermal decomposition of the product. Built into the upper portion of column 33 is column dephlegmator condenser 46 which is used to cool the vapor and condense most of the THF as internal reflux. Two 2-stage blowers, 48 and 50 compress the ammonia vapor sufficiently (about 35 psig) to allow condensation and cooling with refrigerated Dowtherm® J coolant. This liquid ammonia/THF stream is then routed directly back to reactor 30.

Inorganic Phase Dilution

Typically, the inorganic phase (chiefly composed of ammonia and ammonium chloride) is first diluted with water and stored in storage tank 56, analyzed, and batch transferred to a railcar 58 prior to shipment. Preferably, the water added is proportioned to yield a co-product solution containing about 25% water, about 38% dissolved ammonium chloride and about 37% ammonia, which is a useful industrial product mixture. In order to suit specific industrial uses for the ammonia and ammonium chloride co-products, the amount of water added can be varied, and in fact, the addition of water can be entirely eliminated if desired.

As described in commonly-owned copending U.S. application Ser. No. 08/786,536 filed Jan. 21, 1997, all disclosure of which is incorporated herein by reference, it is desirable to inhibit the above aqueous solution of ammonia and ammonium chloride against ferrous metal corrosion by dissolving therein a ferrous metal corrosion-inhibiting amount of at least one water-soluble salt or oxide of zinc, aluminum, arsenic, antimony or bismuth, such as $Bi_2O_3$, ZnO, $ZnCl_2$, $AlCl_3$, and $Al_2O_3$. It is believed that corrosion by the uninhibited solutions is due to the presence of trace amounts of one or more impurities remaining in the solution, which impurities are probably, but not necessarily, one or more sulfur-containing impurities. Amounts of 1000 ppm (wt/wt) of such inhibitors have proven very effective, but any corrosion-inhibiting amount consistent with end-product usage and specifications can be employed.

Wiped-film Evaporation, Nitrogen Strip and Optional Dilution

The concentrated BTPT/THF/TEA solution from feed drum 42 is fed (by flow control) to wiped-film evaporator 44, to remove most of the remaining THF and TEA solvents. Wiped-film evaporator 44 is operated at about 110 mm Hg absolute and 95° C., producing a bottoms product containing <2% residual solvents. The solvent vapors from wiped-film evaporator 44 are condensed in heat exchanger 62, and the condensed solvent is recycled to recycle solvent tank 12 via pump 64. The bottoms product (predominately BTPT) from wiped-film evaporator 44 is fed (by level control on the bottoms receiver pot and pump 66) directly to the upper portion of nitrogen stripping column 68, in which hot nitrogen (about 65° C., atmospheric pressure) is passed upwardly in countercurrent flow to the down-flow product stream to further reduce the small residual solvent content of the BTPT to about 0.5% maximum. This neat product stream is then gravity fed into storage vessel 70 in which, if desired, it can be mixed with one or more solvents for storage and ultimate shipment.

As described in commonly-owned copending U.S. application Ser. No. 08/786,535 filed Jan. 21, 1997, all disclosure of which is incorporated herein by reference, it is highly advantageous to use a wiped-film evaporator operated at a suitable temperature in the range of about 60° to about 140° C., and at a suitable pressure higher than about 40–200 torr absolute (preferably about 100° to about 130° C. at 50–150 torr absolute) for separating most of the remaining solvents from the BTPT/THF/TEA solution. Use of wiped-film evaporator operated under such suitable conditions avoids solids formation on the heating surface of the wiped-film evaporator, and successfully overcomes problems associated with the recovery of N-alkylthiophosphoric triamides from tetrahydrofuran-triethylamine solutions, especially thermal degradation of the triamide product, while at the same time providing a separation process which not only is ideally-suited for large scale commercial operation but which, in addition, actually improves the efficiency of the product recovery step itself.

We claim:

1. A process for separating ammonium chloride from a triamide of the formula $(H)(R)N-P(=Y)(NH_2)_2$, where R is a hydrocarbyl group and Y is an atom of oxygen or sulfur, which process comprises forming a substantially anhydrous mixture which comprises ammonium chloride, said triamide, and ammonia, the ammonia being present in a sufficient excess amount relative to the ammonium chloride to form a separate liquid phase in which the ammonium chloride is dissolved, and separating said liquid phase from the remainder of said mixture.

2. A process according to claim 1 wherein said mixture further includes one or more substantially anhydrous organic solvents.

3. A process according to claim 1 wherein said mixture is formed by mixing said excess of ammonia with the ammonium chloride and said triamide.

4. A process according to claim 2 wherein said mixture is formed by co-producing the ammonium chloride and said triamide in the presence of (i) said excess of ammonia and (ii) at least one or more substantially anhydrous organic solvents.

5. A process according to claim 2 wherein said mixture is formed by mixing said excess of ammonia with the ammonium chloride, said triamide, and at least one or more substantially anhydrous organic solvents.

6. A process according to claim 1 wherein R is an alkyl group and Y is a sulfur atom.

7. A process according to claim 1 wherein said triamide is N-n-butylthiophosphoric triamide.

8. A process according to claim 6 wherein said mixture further includes one or more substantially anhydrous organic solvents.

9. A process according to claim 6 wherein said mixture is formed by mixing said excess of ammonia with the ammonium chloride and said triamide.

10. A process according to claim 8 wherein said mixture is formed by co-producing the ammonium chloride and said triamide in the presence of (i) said excess of ammonia and (ii) at least one or more substantially anhydrous organic solvents.

11. A process according to claim 8 wherein said mixture is formed by mixing said excess of ammonia with the ammonium chloride, said triamide, and at least one or more substantially anhydrous organic solvents.

12. A process according to claim 1 wherein the amount of excess ammonia relative to the ammonium chloride is equivalent to at least about 2.8–10 moles of ammonia per mole of ammonium chloride, and wherein the temperature of said mixture is maintained above about 6° C. but below the temperature at which the triamide undergoes significant thermal degradation.

13. A process according to claim 4 wherein the amount of excess ammonia relative to the ammonium chloride is equivalent to at least 2.8–10 moles of ammonia per mole of ammonium chloride, and wherein the temperature of said mixture is maintained above about 6° C. but below the temperature at which the triamide undergoes significant thermal degradation.

14. A process according to claim 4 wherein the amount of excess ammonia relative to the ammonium chloride is equivalent to at least 2.8–10 moles of ammonia per mole of ammonium chloride, and wherein the temperature of said mixture is maintained at or below 6° C. during the co-production of the triamide and the ammonium chloride, and wherein after completion of formation of the triamide and ammonium chloride, the resulting mixture is heated above about 6° C. but below the temperature at which the triamide undergoes significant thermal degradation to melt the solid ammonia/ammonium chloride complex and thereby form said separate liquid phase.

15. A process according to claim 10 wherein the amount of excess ammonia relative to the ammonium chloride is equivalent to at least 2.8–10 moles of ammonia per mole of ammonium chloride, and wherein the temperature of said mixture is maintained above about 6° C. but below the temperature at which the triamide undergoes significant thermal degradation.

16. A process according to claim 10 wherein the amount of excess ammonia relative to the ammonium chloride is equivalent to at least 2.8–10 moles of ammonia per mole of ammonium chloride, and wherein the temperature of said mixture is maintained at or below 6° C. during the co-production of the triamide and the ammonium chloride, and wherein after completion of formation of the triamide and ammonium chloride, the resulting mixture is heated above about 6° C. but below the temperature at which the triamide undergoes significant thermal degradation to melt the solid ammonia/ammonium chloride complex and thereby form said separate liquid phase.

17. A process according to claim 15 wherein the alkyl group, R, of said triamide has in the range of 2 to 6 carbon atoms.

18. A process according to claim 17 wherein said triamide is N-n-butylthiophosphoric triamide.

19. A process for the preparation of N-hydrocarbylphosphoric triamide or N-hydrocarbylthiophosphoric triamide, which process comprises:

a) mixing in at least one inert liquid organic solvent, and in the presence of a tertiary amine, (i) N-hydrocarbylaminophosphoryl dichloride or N-hydrocarbylaminothiophosphoryl dichloride and (ii) ammonia in proportions (1) that are at least about 16 moles of ammonia per mole of said dichloride, (2) that produce a reaction mixture containing N-hydrocarbylphosphoric triamide or N-hydrocarbylthiophosphoric triamide, and (3) that keep in solution as a separate liquid phase substantially all of the ammonium chloride co-product formed in the reaction, and removing heat of reaction from the mixture so-formed at a rate of removal such that the temperature of the reaction mixture remains high enough to keep ammonium chloride-ammonia complex from forming an appreciable amount of solid phase in said reaction mixture, but low enough to avoid significant reduction in yield of N-hydrocarbylthiophosphoric triamide; and b) separating said separate liquid phase from the remainder of said mixture.

20. A process according to claim 19 wherein said liquid organic solvent boils at one or more temperatures in the range of about 40° to about 120° C. at ordinary atmospheric pressures, wherein said tertiary amine is triethylamine, and wherein said N-hydrocarbylaminophosphoryl dichloride or N-hydrocarbylaminothiophosphoryl dichloride is an N-hydrocarbylaminothiophosphoryl dichloride.

21. A process according to claim 19 wherein said liquid organic solvent is predominately tetrahydrofuran.

* * * * *